United States Patent
Fauran et al.

[11] 3,978,055
[45] Aug. 31, 1976

[54] ARYLAMINO PYRIMIDINIC DERIVATIVES

[75] Inventors: Claude P. Fauran, Paris; Guy R. Bourgery, Colombes; Guy M Raynaud, Paris; Claude J. Gouret, Meudon, all of France

[73] Assignee: Delalande S.A., Courbevoie, France

[22] Filed: Sept. 3, 1974

[21] Appl. No.: 502,285

[30] Foreign Application Priority Data
Sept. 20, 1973 France............................ 73.33831
Mar. 26, 1974 France............................ 74.10327

[52] U.S. Cl.................. 260/247.5 D; 260/256.4 N; 424/248; 424/251
[51] Int. Cl.². ...................................... C07D 239/42
[58] Field of Search............. 260/247.5 D, 256.4 R, 260/256.4 N

[56] References Cited
UNITED STATES PATENTS
3,321,478  5/1967  English .................. 260/256.4 N OTHER PUBLICATIONS
Chkhikvadze et al., C.A. 71:81300p, (1969).

Primary Examiner—Lorraine A. Weinberger
Assistant Examiner—Michael Shippen
Attorney, Agent, or Firm—Woodhams, Blanchard and Flynn

[57] ABSTRACT
Compounds of the formula

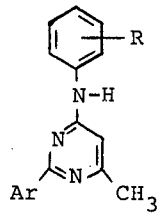

wherein Ar is phenyl or phenyl substituted by one or more halogens, by a trifluoromethyl or a methylenedioxy, by one or more methoxy, by an alkyl having one to 4 carbon atoms or by a dimethylamino,
and R is

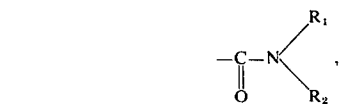

or —O—

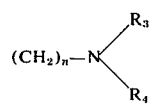

or

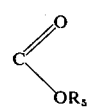

wherein $R_1$ and $R_2$ each are hydrogen or alkyl of 1 to 4 carbon atoms, or

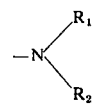

is pyrrolidino, morpholino, piperidino or piperazino N'-substituted by alkyl of 1 to 4 carbon atoms, or phenyl; $R_3$ and $R_4$ each are alkyl of 1 to 3 carbon atoms or

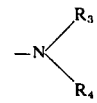

is morpholino, pyrrolidino, piperidino or hexamethyleneimino, n is an integer of 1 to 5; and $R_5$ is alkyl of 1 to 4 carbon atoms, 2,3-dihydroxypropyl or 2,2-dimethyl dioxolan-4-yl methyl or hydroxycarbonylmethyl.

The compounds are obtained by reacting 2-Ar-2-chloro-6-methyl pyrimidine, with

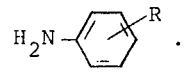

The compounds possess sedative, antiinflammatory, antiulcerous, vasodilatatory, antibronchoconstrictive, anticholinergic, diuretic, spasmolytic, cardiac analeptic, analgesic and myorelaxant properties.

10 Claims, No Drawings

ARYLAMINO PYRIMIDINIC DERIVATIVES

The present invention relates to novel arylamino pyrimidinic derivatives, their process of preparation and their therapeutic application.

The novel derivatives according to the invention correspond to the general formula:

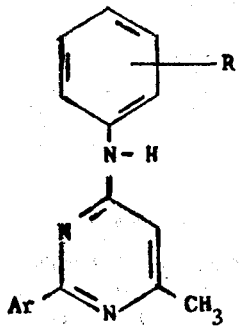

in which:

Ar represents an unsubstituted phenyl ring or a phenyl ring substituted by one or more halogen atoms, by a trifluoromethyl or a methylene dioxy group, by one or more methoxy groups, by an alkyl radical containing up to 4 carbon atoms or by a dimethylamino group; and R represents: a carboxamidic group of formula:

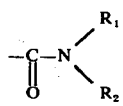

in which $R_1$ and $R_2$ each represent a hydrogen atom or an alkyl radical containing up to 4 carbon atoms, or form together with the nitrogen atom to which they are attached a heterocyclic ring selected from the following: pyrrolidino, morpholino, piperidino or piperazino N'-substituted by an alkyl radical containing up to 4 carbon atoms or by a phenyl ring, or an amino alkoxy chain of formula:

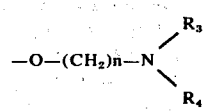

in which $R_3$ and $R_4$ each represent an alkyl radical containing 1 to 3 carbon atoms, or may form togerher with the nitrogen atom to which they are attached, a heterocyclic ring selected from the following: morpholino, pyrrolidino, piperidino and hexamethyleneimino, n being an integer of from 1 to 5, or an alkoxycarbonyl group of formula

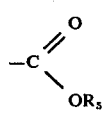

in which $R_5$ represents an alkyl radical containing up to 4 carbon atoms, a 2,3-dihydroxypropyl radical or a 2,2-dimethyl dioxolan -4-yl methyl radical, or a hydroxycarbonylmethyl radical.

The process according to the invention consists in condensing in acetic acid and in the presence of hydrochloric acid, a 2-aryl-4-chloro-6-methyl pyrimidine of the general formula:

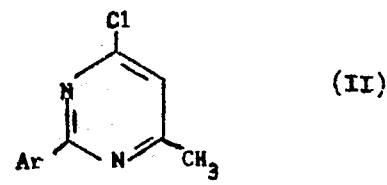

in which:

Ar represents an unsubstituted phenyl ring or a phenyl ring substituted by one or more halogen atoms, by a trifluoromethyl or a methylene dioxy group, by one or more methoxy groups, by an alkyl radical containing up to 4 carbon atoms or by a dimethylamino group, with an anilino derivative of the general formula:

in which R' represents: a carboxamidic group of formula

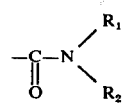

in which: $R_1$ and $R_2$ each represent a hydrogen atom or an alkyl radical containing up to 4 carbon atoms, or form together with the nitrogen atom to which they are attached, a heterocyclic ring selected from the following: pyrrolidino, morpholino, piperidino or piperazino N'-substituted by an alkyl radical containing up to 4 carbon atoms or by a phenyl ring, or an amino alkoxy chain of formula

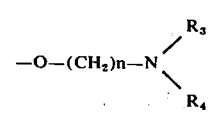

in which $R_3$ and $R_4$ each represent an alkyl radical containing 1 to 3 carbon atoms, or may form, together with the nitrogen atom to which they are attached, a heterocyclic ring selected from the following: morpholino, pyrrolidino, piperidino and hexamethyleneimino, n being an integer of from 1 to 5, or an alkoxycarbonyl group of formula

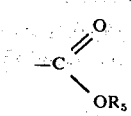

in which $R_5$ represents an alkyl radical containing up to 4 carbon atoms, or a hydroxycarbonylmethyl radical, to produce a derivative corresponding to the general formula:

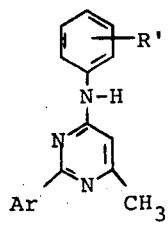

(I')

and, on occasion, to subject a derivative of formula I', in which R' represents a methoxycarbonyl group, to a transesterification process in the presence of sodium with 2,2-dimethyl-4' hydroxymethyl-1,3-dioxolane to produce a derivative of formula:

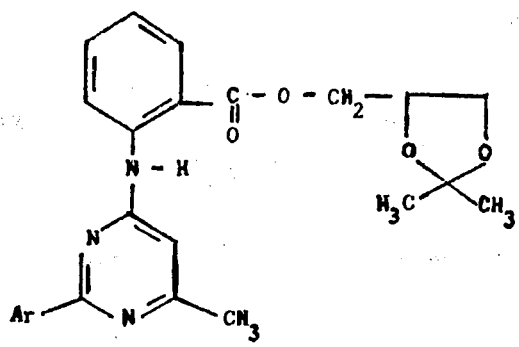

which may then be transformed into a derivative of formula:

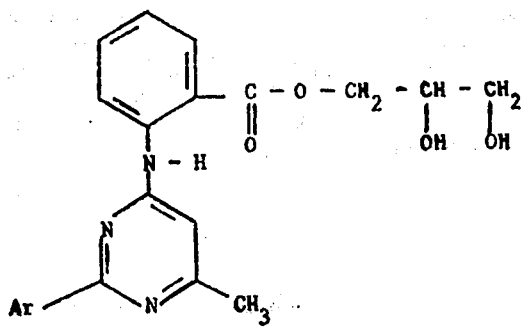

by opening of the dioxolane ring by the action of 2N hydrochloric acid.

The following preparations are given by way of example to illustrate the invention.

EXAMPLE 1

2-(3',4',5'- trimethoxy phenyl)-4-(para pyrrolidino carbonyl phenylamino) -6-methyl pyrimidino (Code No. 72271)

A mixture of 44.2g of 2-(3',4',5'-trimethoxy phenyl)-4-chloro-6-methyl pyrimidine and 28.6 g of 4 - pyrrolidino carbonyl anilino in 300 c.c. of acetic acid in the presence of 0.45 cc of concentrated hydrochloric acid is heated at 80°C for 40 minutes. After cooling, the solution is diluted with 2.5 l of water and alkalinised with ammonia.

The precipitate formed is filtered, washed with water and recrystallized from ethyl acetate.

Melting point = 210°C Yield = 71%

Empirical formula = $C_{25}H_{28}N_4O_4$

Elementary analysis:

|  | C | H | N |
|---|---|---|---|
| Calculated % | 66.94 | 6.29 | 12.49 |
| Found % | 66.85 | 6.40 | 12.49 |

EXAMPLE 2

2 - (3' - trifluoromethylphenyl)-4- [ortho ($\beta$, $\gamma$-dihydroxy propoxycarbonyl) phenyl amino] -6-methyl pyrimidine.

(Code No: 72 502)

1st stage N - [2-(3'-trifluoromethylphenyl)- 6-methyl-4-pyrimidyl]methyl anthranilate.

(Code No: 72 437)

This derivative is obtained by the mode of operation described in Example 1 the recrystallisation being carried out in isopropyl alcohol and not ethyl acetate.

Melting point = 111°C Yield = 86%

Empirical formula = $C_{20}H_{16}F_3N_3O_2$

Elementary analysis:

|  | C | H | N |
|---|---|---|---|
| Calculated % | 62.01 | 4.16 | 10.85 |
| Found % | 62.06 | 4.21 | 10.76 |

2nd stage N-[2-(3'trifluoromethyl phenyl) -6-methyl-4-pyrimidyl](2",2" -dimethyl dioxolan -4"-yl) methyl anthranilate.

(Code No. 72 495)

500 c.c of 2,2 - dimethyl -4-hydroxymethyl dioxolane and then 0.6 g. of sodium are introduced into a reaction vessel which has previously been purged with nitrogen. The vessel is warmed just until total dissolution of the sodium is effected. After returning to ambient temperature, 162 g of N-[2-(3'-trifluoromethyl phenyl)-6-methyl -4-pyrimidyl] methyl anthanilate, of code No. 72 437 obtained in the preceding stage, is introduced into the reaction vessel. The mixture is heated for 5 hours at 145°C, under nitrogen, the methanol formed during the course of the reaction being distilled off. After cooling, the solution obtained is diluted with 3 liters of water. The precipitate formed is filtered, washed with water and recrystallised from ethanol.

Melting point = 107°C Yield = 80%

Empirical formula = $C_{25}H_{24}F_3N_3O_4$

Molecular weight = 487.46

Elementary analysis:

|  | C | H | N |
|---|---|---|---|
| Calculated % | 61.59 | 4.96 | 8.62 |
| Found % | 61.64 | 5.04 | 8.77 |

3rd stage 2-(3'-trifluoromethyl phenyl)-4- ortho (ξ,γ-dihydroxy propoxycarbonyl) phenylamino]-6-methyl pyrimidine
(Code No. 72 502)

A suspension of 111.8g of N-[2-(3'-trifluoromethyl-phenyl)-6-methyl-4-pyrimidyl] (2'',2''-dimethyl dioxolan-4''-yl) methyl anthranilate of code No. 72 495 obtained in the preceding stage, in 750 c.c of 2N hydrochloric acid is heated for 20 minutes under reflux.

After cooling, the precipitate obtained is filtered, washed with water, dissolved in 1 l of 50% alcohol and neutralised with triethylamine. The solution is concentrated the residue is taken up in 1 l of water, the precipitate is filtered, washed with water and recrystallised from ethanol Melting point = 154°C  Yield = 74%
Empirical formula = $C_{22}H_{20}F_3N_3O_4$
Elementary analysis:

|  | C | H | N |
|---|---|---|---|
| Calculated % | 59.06 | 4.51 | 9.39 |
| Found % | 59.10 | 4.64 | 9.51 |

The derivatives listed in the following Table I have been prepared by the same mode of operation.

TABLE I

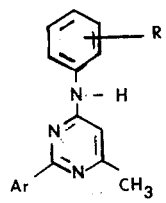

| Code No. | Ar | R | Empirical formula | Molecular weight | Melting point (°C) | Yield (%) | Elementary analysis C | H | N |
|---|---|---|---|---|---|---|---|---|---|
| 72 327 | Cl—⟨⟩— | (H₃C)₂N-C(O)—⟨⟩— | $C_{20}H_{19}ClN_4O$ | 366.84 | 232 | 30 | Calculated % 65.48  Found (%) 65.36 | 5.22  5.17 | 15.27  15.18 |
| 72 255 | " | pyrrolidinyl-C(O)—⟨⟩— | $C_{22}H_{21}ClN_4O$ | 392.88 | 242 | 50 | Calculated (%) 67.25  Found (%) 67.10 | 5.39  5.25 | 14.24  14.10 |
| 72 256 | " | morpholinyl-C(O)—⟨⟩— | $C_{22}H_{21}ClN_4O_2$ | 408.38 | 220 | 50 | Calculated (%) 64.62  Found (%) 64.51 | 5.18  4.98 | 13.70  13.51 |
| 72 276 | " | piperidinyl-C(O)—⟨⟩— | $C_{23}H_{23}ClN_4O$ | 406.90 | 238 | 38 | Calculated (%) 67.89  Found (%) 67.89 | 5.70  5.90 | 13.77  13.61 |
| 72 292 | " | H₃C-N(piperazinyl)-C(O)—⟨⟩— | $C_{23}H_{24}ClN_5O$ | 421.92 | 215 | 27 | Calculated (%) 65.47  Found (%) 65.35 | 5.73  5.58 | 16.60  16.67 |
| 72 260 | " | C₆H₅-N(piperazinyl)-C(O)—⟨⟩— | $C_{28}H_{26}ClN_5O$ | 479.99 | 230 | 54 | Calculated (%) 69.48  Found % 69.40 | 5.42  5.25 | 14.47  14.27 |
| 72 257 | " | H₂N-C(O)—⟨⟩— | $C_{18}H_{15}ClN_4O$ | 338.79 | 234 | 68 | Calculated % 63.81  Found (%) 63.96 | 4.46  4.53 | 16.54  16.35 |
| 72 311 | " | H₂N-C(O)—⟨⟩— | $C_{18}H_{15}ClN_4O$ | 338.79 | 228 | 58 | Calculated (%) 63.81  Found (%) 63.65 | 4.46  4.56 | 16.54  16.51 |
| 72 283 | " | H₅C₂O-C(O)—⟨⟩— | $C_{20}H_{18}ClN_3O_2$ | 367.82 | 180 | 84 | Calculated (%) 65.30  Found (%) 65.50 | 4.93  5.13 | 11.42  11.22 |
| 71 442 | " | H₃CO-C(O)—⟨⟩— | $C_{19}H_{16}ClN_3O_2$ | 353.79 | 150 | 40 | Calculated (%) 64.50  Found (%) 64.30 | 4.56  4.38 | 11.88  11.91 |

TABLE I-continued

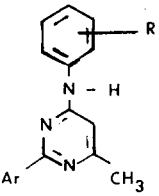

| Code No. | Ar | R | Empirical formula | Molecular weight | Melting point (°C) | Yield (%) | Elementary analysis | | |
|---|---|---|---|---|---|---|---|---|---|
| | | | | | | | | C | H | N |
| 71 488 | " | H₃C–O\\_/O–CH₂–O–CO–⌬– | $C_{24}H_{24}ClN_3O_4$ | 453.91 | 139 | 50 | Calculated (%) Found (%) | 63.50 63.60 | 5.33 5.42 | 9.26 9.15 |
| 71 530 | " | CH₂–CH–CH₂–O–CO–⌬– (HO OH) | $C_{21}H_{20}ClN_3O_4$ | 413.85 | 173 | 50 | Calculated (%) Found (%) | 60.94 60.84 | 4.87 4.94 | 10.15 10.26 |
| 72 755 | F–⌬– | ⌖N–CO–⌬– | $C_{22}H_{21}FN_4O$ | 376.42 | 246 | 33 | Calculated (%) Found (%) | 70.19 70.16 | 5.62 5.56 | 14.89 14.95 |
| 72 754 | " | O⌖N–CO–⌬– | $C_{22}H_{21}FN_4O_2$ | 392.42 | 187 | 71 | Calculated (%) Found (%) | 67.33 67.53 | 5.39 5.33 | 14.28 14.38 |
| 72 741 | " | ⌖N–CO–⌬– | $C_{23}H_{23}FN_4O$ | 390.45 | 214 | 66 | Calculated (%) Found (%) | 70.75 70.55 | 5.94 5.90 | 14.35 14.38 |
| 72 783 | " | H₂N–CO–⌬– | $C_{18}H_{15}FN_4O$ | 322.33 | 224 | 72 | Calculated (%) Found (%) | 67.07 66.87 | 4.69 4.87 | 17.38 17.28 |
| 72 773 | " | H₂N–CO–⌬– | $C_{18}H_{15}FN_4O$ | 322.33 | 219 | 55 | Calculated (%) Found (%) | 67.07 67.17 | 4.69 4.66 | 17.38 17.45 |
| 72 778 | " | H₅C₂O–CO–⌬– | $C_{20}H_{18}FN_3O_2$ | 351.38 | 168 | 82 | Calculated (%) Found (%) | 68.36 68.37 | 5.16 5.13 | 11.96 12.06 |
| 72 772 | " | H₃CO–CO–⌬– | $C_{19}H_{16}FN_3O_2$ | 337.34 | 119 | 88 | Calculated (%) Found (%) | 67.64 67.80 | 4.80 4.79 | 12.46 12.30 |
| 72 796 | " | H₃C–O\\_/O–CH₂–O–CO–⌬– | $C_{24}H_{24}FN_3O_4$ | 437.46 | 105 | 63 | Calculated (%) Found (%) | 65.89 65.86 | 5.53 5.42 | 9.61 9.59 |
| 72 826 | " | CH₂–CH–CH₂–O–CO–⌬– (OH OH) | $C_{21}H_{20}FN_3O_4$ | 397.39 | 143 | 31 | Calculated (%) Found (%) | 63.47 63.43 | 5.07 5.01 | 10.57 10.73 |
| 730234 | " | HO–CO–CH₂–⌬– | $C_{19}H_{16}FN_3O_2 + \frac{1}{2}H_2O$ | 346.35 | 179 | 50 | (%) Found (%) | 65.88 66.03 | 4.95 4.76 | 12.13 12.02 |

TABLE I-continued

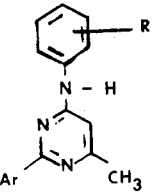

| Code No. | Ar | R (structure) | Empirical formula | Molecular weight | Melting point (°C) | Yield (%) | Elementary analysis | C | H | N |
|---|---|---|---|---|---|---|---|---|---|---|
| 72 473 | 3-CF$_3$-C$_6$H$_4$ | pyrrolidinyl-CO-C$_6$H$_4$- | C$_{23}$H$_{21}$F$_3$N$_4$O | 426.43 | 206 | 55 | Calculated (%)<br>Found (%) | 64.78<br>64.74 | 4.96<br>4.76 | 13.14<br>13.21 |
| 72 420 | " | morpholinyl-CO-C$_6$H$_4$- | C$_{23}$H$_{21}$F$_3$N$_4$O$_2$ | 442.43 | 193 | 65 | Calculated (%)<br>Found (%) | 62.44<br>62.26 | 4.78<br>4.80 | 12.66<br>12.50 |
| 72 421 | " | piperidinyl-CO-C$_6$H$_4$- | C$_{24}$H$_{23}$F$_3$N$_4$O | 440.46 | 204 | 51 | Calculated (%)<br>Found (%) | 65.44<br>65.33 | 5.26<br>5.29 | 12.72<br>12.72 |
| 72 503 | " | C$_6$H$_5$-N-piperazinyl-CO-C$_6$H$_4$- | C$_{29}$H$_{26}$F$_3$N$_5$O | 517.54 | 198 | 27 | Calculated (%)<br>Found (%) | 67.30<br>67.29 | 5.06<br>5.26 | 13.51<br>13.33 |
| 72 419 | " | H$_2$N-CO-C$_6$H$_4$- | C$_{19}$H$_{15}$F$_3$N$_4$O | 372.34 | 193 | 81 | Calculated (%)<br>Found (%) | 61.29<br>61.20 | 4.06<br>4.20 | 15.05<br>15.03 |
| 72 432 | " | H$_2$N-CO-C$_6$H$_4$- | C$_{19}$H$_{15}$F$_3$N$_4$O | 372.34 | 180 | 83 | Calculated (%)<br>Found (%) | 61.29<br>61.46 | 4.06<br>3.88 | 15.05<br>14.83 |
| 72 505 | " | H$_5$C$_2$O-CO-C$_6$H$_4$- | C$_{21}$H$_{18}$F$_3$N$_3$O$_2$ | 401.38 | 260 | 71 | Calculated (%)<br>Found (%) | 62.84<br>62.87 | 4.58<br>4.67 | 10.47<br>10.56 |
| 72 623 | 3,4-methylenedioxyphenyl | pyrrolidinyl-CO-C$_6$H$_4$- | C$_{23}$H$_{22}$N$_4$O$_3$ | 402.44 | 225 | 69 | Calculated (%)<br>Found (%) | 68.64<br>68.46 | 5.51<br>5.60 | 13.92<br>13.78 |
| 72 621 | " | morpholinyl-CO-C$_6$H$_4$- | C$_{23}$H$_{22}$N$_4$O$_4$ | 418.44 | 260 | 31 | Calculated (%)<br>Found (%) | 66.01<br>65.97 | 5.30<br>5.35 | 13.39<br>13.22 |
| 72 687 | " | piperidinyl-CO-C$_6$H$_4$- | C$_{24}$H$_{24}$N$_4$O$_3$ | 416.46 | 248 | 78 | Calculated (%)<br>Found (%) | 69.21<br>69.30 | 5.81<br>5.80 | 13.45<br>13.27 |
| 72 608 | " | H$_2$N-CO-C$_6$H$_4$- | C$_{19}$H$_{16}$N$_4$O$_3$ | 348.35 | 210 | 51 | Calculated (%)<br>Found (%) | 65.51<br>65.43 | 4.63<br>4.69 | 16.08<br>16.03 |
| 730025 | " | H$_2$N-CO-C$_6$H$_4$- | C$_{19}$H$_{16}$N$_4$O$_3$ | 348.35 | 243 | 45 | Calculated (%)<br>Found (%) | 65.51<br>65.27 | 4.63<br>4.70 | 16.08<br>16.05 |
| 72 613 | " | H$_5$C$_2$O-CO-C$_6$H$_4$- | C$_{21}$H$_{19}$N$_3$O$_4$ | 377.39 | 180 | 83 | Calculated (%)<br>Found (%) | 66.83<br>66.67 | 5.07<br>5.12 | 11.14<br>11.33 |
| 72 665 | " | H$_3$CO-CO-C$_6$H$_4$- | C$_{20}$H$_{17}$N$_3$O$_4$ | 363.36 | 163 | 87 | Calculated (%)<br>Found (%) | 66.11<br>66.05 | 4.72<br>4.88 | 11.57<br>11.57 |

TABLE I-continued

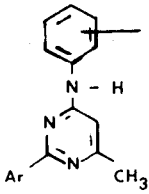

| Code No. | Ar | R | Empirical formula | Molecular weight | Melting point (°C) | Yield (%) | Elementary analysis | | | |
|---|---|---|---|---|---|---|---|---|---|---|
| | | | | | | | | C | H | N |
| 72 701 | 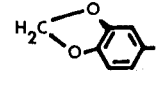 | 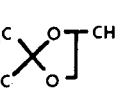 | $C_{25}H_{25}N_3O_6$ | 463,48 | 149 | 59 | Calculated (%) Found (%) | 64,78 64,98 | 5,44 5,36 | 9,07 9,23 |
| 72 686 | '' | 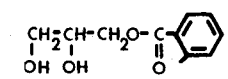 | $C_{22}H_{21}N_3O_6$ | 423,41 | 161 | 73 | Calculated (%) Found (%) | 62,40 62,60 | 5,00 4,98 | 9,93 9,92 |
| 72 536 | 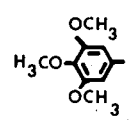 | 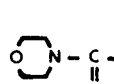 | $C_{25}H_{28}N_4O_5$ | 464,51 | 206 | 72 | Calculated (%) Found (%) | 64,64 64,50 | 608 6,15 | 12,06 11,98 |
| 72 317 | '' | 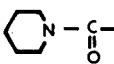 | $C_{26}H_{30}N_4O_4$ | 462,53 | 217 | 59 | Calculated (%) Found (%) | 67,51 67,42 | 6,54 6,52 | 12,11 11,91 |
| 72 462 | '' | 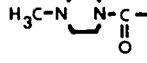 | $C_{26}H_{31}N_5O_4$ | 477,59 | 190 | 37 | Calculated (%) Found (%) | 65,39 65,38 | 6,54 6,66 | 14,67 14,54 |
| 72 450 | '' | 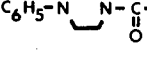 | $C_{31}H_{33}N_5O_4$ | 539,61 | 230 | 42 | Calculated (%) Found (%) | 69,00 68,80 | 6,16 6,24 | 12,98 12,84 |
| 72 442 | 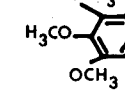 | 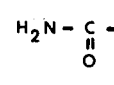 | $C_{21}H_{22}N_4O_4$ | 394.42 | 190 | 54 | Calculated (%) Found (%) | 63.94 63.94 | 5.62 5.71 | 14.21 14.11 |
| 72 417 | '' | 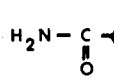 | $C_{21}H_{22}N_4O_4$ | 394.42 | 212 | 46 | Calculated (%) Found (%) | 63.94 63.74 | 5.62 5.66 | 14.21 14.19 |
| 72 247 | '' | 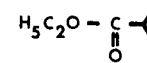 | $C_{23}H_{25}N_3O_5$ | 423,45 | 210 | 81 | Calculated (%) Found (%) | 65.23 65.27 | 5.95 5.98 | 9.93 9.87 |
| 72 479 | '' | 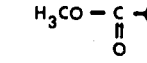 | $C_{22}H_{23}N_3O_5$ | 409.43 | 121 | 52 | Calculated (%) Found (%) | 64.53 64.74 | 5.66 5.65 | 10.26 10.31 |
| 71 510 | '' | 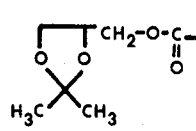 | $C_{27}H_{31}N_3O_7$ | 509.54 | 118 | 56 | Calculated (%) Found (%) | 63.64 64,84 | 6.13 6.02 | 8.25 8.34 |

TABLE I-continued

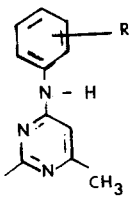

| Code No. | Ar | R (on phenyl) | | Empirical formula | Molecular weight | Melting point (°C) | Yield (%) | Elementary analysis | C | H | N |
|---|---|---|---|---|---|---|---|---|---|---|---|
| 730136 | C₆H₅- | -C₆H₄-O-CH₂-CH₂-N(CH₃)₂ | base | C₂₁H₂₄N₄O | 348.43 | 155 | 94 | Calculated % Found % | 72.38 72.53 | 6.94 6.86 | 16.08 16.39 |
| 730282 | C₆H₅- | -C₆H₄-O-CH₂-CH₂-N(C₃H₇(n))₂ | hydrochloride | C₂₅H₃₃ClN₄O | 441.00 | 220 | 67 | Calculated % Found % | 68.08 67.95 | 7.54 7.74 | 12.71 12.86 |
| 730218 | C₆H₅- | -C₆H₄-O-CH₂-CH₂-N(pyrrolidine) | base | C₂₃H₂₆N₄O | 374.47 | 157 | 77 | Calculated % Found % | 73.77 73.88 | 7.00 7.09 | 14.96 14.54 |
| 730221 | C₆H₅- | -C₆H₄-O-CH₂-CH₂-N(piperidine) | base | C₂₄H₂₈N₄O | 388.50 | 130 | 51 | Calculated % Found % | 74.19 74.39 | 7.26 7.36 | 14.42 14.22 |
| 730591 | 3,4,5-(H₃CO)₃-C₆H₂- | -C₆H₄-O-CH₂-CH₂-N(CH₃)₂ | base | C₂₄H₃₀N₄O₄ | 438.51 | 133 | 62 | Calculated % Found % | 65.73 65.53 | 6.90 6.95 | 12.78 12.76 |
| 730229 | C₆H₅- | -C₆H₄-O-CH₂-CH₂-N(morpholine) | base | C₂₃H₂₆N₄O₂ | 390.47 | 121 | 57 | Calculated % Found % | 70.74 70.93 | 6.71 6.88 | 14.35 14.15 |
| 730379 | C₆H₅- | -C₆H₄-O-CH₂-CH₂-N(hexamethyleneimine) | hydrochloride | C₂₅H₃₁ClN₄O | 438.99 | 177 | 41 | Calculated % Found % | 68.40 68.25 | 7.12 6.92 | 12.76 12.79 |
| 730225 | 4-Cl-C₆H₄- | -C₆H₄-O-CH₂-CH₂-N(CH₃)₂ | base | C₂₁H₂₃ClN₄O | 382.88 | 129 | 53 | Calculated % Found % | 65.87 66.07 | 6.06 6.26 | 14.63 14.64 |
| 730241 | 3-CF₃-C₆H₄- | -C₆H₄-O-CH₂-CH₂-N(CH₃)₂ | base | C₂₂H₂₃F₃N₄O | 416.44 | 132 | 48 | Calculated % Found % | 63.44 63.58 | 5.57 5.68 | 13.46 13.56 |
| 730243 | 3-CF₃-C₆H₄- | -C₆H₄-O-CH₂-CH₂-N(pyrrolidine) | base | C₂₄H₂₅F₃N₄O | 442.47 | 133 | 75 | Calculated % Found % | 65.14 65.33 | 5.70 5.70 | 12.66 12.85 |
| 730224 | 3-F-C₆H₄- | -C₆H₄-O-CH₂-CH₂-N(CH₃)₂ | base | C₂₁H₂₃FN₄O | 366.43 | 167 | 55 | Calculated % Found % | 68.63 68.94 | 6.33 6.53 | 15.29 15.37 |
| 730231 | 3-F-C₆H₄- | -C₆H₄-O-CH₂-CH₂-N(piperidine) | base | C₂₄H₂₇FN₄O | 406.49 | 140 | 68 | Calculated % Found % | 70.91 71.09 | 6.70 6.86 | 13.73 13.66 |

TABLE I-continued

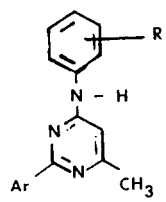

| Code No. | Ar | R | Empirical formula | Molecular weight | Melting point (°C) | Yield (%) | Elementary analysis | | | |
|---|---|---|---|---|---|---|---|---|---|---|
| | | | | | | | | C | H | N |
| 730262 | 3-Cl-C₆H₄ | -C₆H₄-O-CH₂-CH₂-N(CH₃)₂ | base | C₂₁H₂₃ClN₄O | 382.89 | 136 | 50 | Calculated % | 65.87 | 6.06 | 14.63 |
| | | | | | | | | Found % | 66.04 | 6.26 | 14.58 |
| 730283 | 2-Cl-C₆H₄ | -C₆H₄-O-CH₂-CH₂-N(hexamethyleneimino) | base | C₂₅H₂₉ClN₄O | 436.97 | 126 | 30 | Calculated % | 68.71 | 6.69 | 12.82 |
| | | | | | | | | Found % | 68.78 | 6.91 | 12.98 |
| 730633 | 3,4,5-(OCH₃)₃-C₆H₂ | -C₆H₄-O-CH₂-CH₂-N(morpholino) | base | C₂₆H₃₂N₄O₅ | 480.55 | 129 | 67 | Calculated % | 64.98 | 6.71 | 11.66 |
| | | | | | | | | Found % | 64.77 | 7.28 | 11.60 |
| 730741 | 3,4,5-(OCH₃)₃-C₆H₂ | -CH₃-C₆H₃-O-CH₂-CH₂-N(CH₃)₂ | semi-hydrate + ½ H₂O | C₂₄H₃₀N₄O₄ | 447.52 | 111 | 34 | Calculated % | 64.41 | 6.98 | 12.52 |
| | | | | | | | | Found % | 64.88 | 7.00 | 12.58 |
| 730732 | 4-Cl-C₆H₄ | -C₆H₄-O-CH₂-CH₂-N(morpholino) | base | C₂₃H₂₅ClN₄O₂ | 424.92 | 134 | 73 | Calculated % | 65.01 | 5.93 | 13.19 |
| | | | | | | | | Found % | 64.77 | 5.90 | 13.28 |
| 730695 | 3-Cl-C₆H₄ | -C₆H₄-O-CH₂-CH₂-N(morpholino) | " | C₂₃H₂₅ClN₄O₂ | 424.92 | 134 | 69 | Calculated % | 65.01 | 5.93 | 13.19 |
| | | | | | | | | Found % | 64.78 | 6.02 | 13.24 |
| 730712 | 3-CF₃-C₆H₄ | -C₆H₄-O-CH₂-CH₂-N(morpholino) | " | C₂₄H₂₅F₃N₄O₂ | 458.47 | 132 | 53 | Calculated % | 62.87 | 5.50 | 12.22 |
| | | | | | | | | Found % | 62.79 | 5.51 | 12.40 |
| 730731 | 3,4-methylenedioxy-C₆H₃ | -C₆H₄-O-CH₂-CH₂-N(morpholino) | " | C₂₄H₂₆N₄O₄ | 434.48 | 112 | 72 | Calculated % | 66.34 | 6.03 | 12.90 |
| | | | | | | | | Found % | 66.20 | 5.93 | 12.70 |
| 740023 | 3-F-C₆H₄ | -C₆H₄-O-CH₂-CH₂-N(morpholino) | base | C₂₃H₂₅FN₄O₂ | 408.46 | 128 | 73 | Calculated % | 67.63 | 6.17 | 13.72 |
| | | | | | | | | Found % | 67.86 | 6.15 | 13.60 |
| 740108 | 4-H₃CO-C₆H₄ | -C₆H₄-O-CH₂-CH₂-N(morpholino) | base | C₂₄H₂₈N₄O₃ | 420.50 | 150 | 67 | Calculated % | 68.55 | 6.71 | 13.33 |
| | | | | | | | | Found % | 68.81 | 6.91 | 13.15 |
| 740087 | 4-H₃C-C₆H₄ | -C₆H₄-O-CH₂-CH₂-N(morpholino) | base | C₂₄H₂₈N₄O₂ | 404.50 | 143 | 70 | Calculated % | 71.26 | 6.98 | 13.85 |
| | | | | | | | | Found % | 71.46 | 7.18 | 13.68 |
| 740140 | 4-(CH₃)₂N-C₆H₄ | -C₆H₄-O-CH₂-CH₂-N(morpholino) | base | C₂₅H₃₁N₅O₂ | 433.54 | 163 | 50 | Calculated % | 69.26 | 7.12 | 16.16 |
| | | | | | | | | Found % | 69.16 | 7.37 | 16.06 |

TABLE I-continued

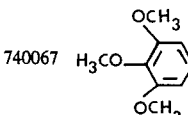

| Code No. | Ar | R | | Empirical formula | Molecular weight | Melting point (°C) | Yield (%) | Elementary analysis | | |
|---|---|---|---|---|---|---|---|---|---|---|
| | | | | | | | | C | H | N |
| 740067 | 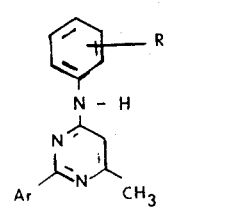 |  | base | $C_{26}H_{32}N_4O_5$ | 480.55 | 142 | 77 | Calculated % 64.98 Found % 64.86 | 6.71 6.91 | 11.66 11.46 |
| 740391 | 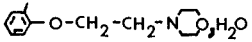 |  | base | $C_{23}H_{28}N_4O_3$ | 408.49 | 372 | 71 | Calculated % 67.62 Found % 67.63 | 6.91 6.86 | 13.72 13.71 |
| 740393 | 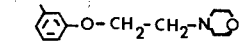 |  | base | $C_{23}H_{26}N_4O_2$ | 390.47 | 123 | 43 | Calculated % 70.74 Found % 70.87 | 6.71 6.81 | 14.35 14.33 |
| 740324 | 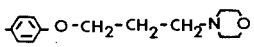 | | base | $C_{24}H_{28}N_4O_2$ | 404.50 | 124 | 75 | Calculated % 71.26 Found % 71.11 | 6.98 7.09 | 13.85 13.78 |

The derivatives of formula I have been tested on animals in the laboratory and have been shown to possess sedative, antiinflammatory, antiulcerous, vasodilatatory, antibronchoconstrictive and anticholinergic, diuretic, spasmolytic, cardiacanaleptic, analgesic and myorelaxant properties, certain of the derivatives possessing hypotensive properties whilst other possess hypertensive properties.

1. Sedative properties

The derivatives of formula I, administered by oral means to the mouse, reduce the number of explorations in the escape enclosure and in an actimeter having luminous beams and photoelectric cells.

By way of example the following Table II lists the percentage diminution in the number of explorations in the escape enclosure, resulting from the administration of 100mg/kg/p.o. of different derivatives of formula I.

TABLE II

| Code No. of derivatives tested | Percentage diminution of number of explorations (%) |
|---|---|
| 71 510 | 40 |
| 72 271 | 40 |
| 72 432 | 35 |
| 72 442 | 60 |
| 72 450 | 35 |
| 72 536 | 75 |
| 72 773 | 45 |
| 72 778 | 35 |
| 730 712 | 32 |
| 730 741 | 30 |

Also, the DE 50 of the derivative of code No. 730 229 is 82mg/kg/p.o. for the test on the number of explorations in the escape enclosure and 120mg/kg/p.o. for the test on the number of explorations in the actimeter.

2. Hypertensive properties

Administered by intraveinous means, the derivatives of formula I provoke an increase in the arterial pressure of an anaosthetised rat.

By way of example, the results obtained by the administration of 2 mg/kg/i.v. of different derivatives of formula I are listed in the following Table III.

TABLE III

| Code Nos. of derivative tested | Percentage augmentation of arterial pressure (%) | Duration of effect (mm) |
|---|---|---|
| 730 712 | 23 | ≃ 30 |
| 730 741 | 27 | ≃ 35 |

3. Antiulcerous properties

The derivatives of formula I, administered by oral means, reduce the extent of gastric ulcers provoked in a rat by tying of the pylorus (Shay ulcers)

Table IV indicated, by way of example, the results obtained by the administration of 50mg/kg/i.d. of different derivatives of formula I.

TABLE IV

| Code No. of derivative tested | Percentage reduction of shay ulcers % |
|---|---|
| 71 510 | 35 |
| 72 255 | 35 |
| 72 257 | 50 |
| 72 260 | 35 |
| 72 276 | 40 |
| 72 311 | 40 |
| 72 317 | 40 |
| 72 417 | 40 |
| 72 432 | 35 |
| 72 502 | 35 |
| 72 613 | 70 |
| 72 621 | 40 |
| 72 687 | 40 |
| 730 225 | 53 |
| 730 231 | 50 |
| 730 283 | 45 |
| 730 282 | 50 |
| 72 754 | 40 |
| 72 773 | 40 |
| 730 025 | 35 |

4. Vasodilatatory properties

The derivatives of formula I are capable of augmenting the flow of the coronary vessels of this isolated heart of a guinea - pig, when said derivatives are added in the perfusion liquid of said organ.

The percentage augmentation of the flow of the isolated heart of the guinea - pig by adding different derivatives of formula I to the perfusion liquid are given by way of example in the following Table V.

TABLE V

| Code No. of derivative tested | Dose administered ($\mu$g/ml) | Percentage augmentation of flow of isolated heart of guinea - pig (%) |
|---|---|---|
| 72 255 | 1 | 45 |
| 72 257 | 1 | 80 |
| 72 260 | 1 | 70 |
| 72 450 | 1 | 85 |
| 72 505 | 1 | 50 |
| 72 613 | 1 | 85 |
| 72 796 | 1 | 60 |
| 730283 | 0.1 | 61 |
| 730241 | 0.5 | 77 |

5. Antibronchoconstrictive and anticholinergic properties

Injected by intraduodenal means, the derivatives of formula I are capable of opposing the bronchoconstriction provoked in the guinea - pig by the intraveinous injection of acetylcholine and evaluated by the Konzett method.

By way of example, the following Table VI lists the percentage inhibition of the bronchoconstriction following the intraperitoneal injection of 100mg/kg of different derivatives of formula I.

TABLE VI

| Code No. of derivative tested | Percentage inhibition of bronchoconstriction (%) |
|---|---|
| 72 255 | 50 |
| 72 276 | 50 |
| 72 311 | 80 |
| 72 502 | 50 |
| 72 608 | 65 |
| 72 826 | 100 |
| 730 025 | 50 |

6. Diuretic properties

The derivatives of formula I, administered by oral means to the mouse, simultaneously with a volume of 1ml of an isotonic solution of sodium chloride per 25g of the corporeal weight of the mouse, are capable of provoking an augmentation of the volume of urine emitted by reference to control animals, the volume being measured for 6 hours following administration.

The following Table VII indicates, by way of example the percentage augmentation of urinary elimination resulting from the administration of 25mg/kg/p.o. of different derivatives of formula I.

TABLE VII

| Code No. of derivative tested | Percentage augmentation of urinary elimination (%) |
|---|---|
| 72 292 | 55 |
| 72 327 | 85 |
| 72 417 | 65 |
| 72 419 | 80 |
| 72 432 | 200 |
| 72 495 | 115 |
| 72 623 | 85 |
| 72 701 | 45 |
| 72 754 | 50 |
| 72 773 | 110 |
| 72 783 | 80 |
| 72 826 | 80 |
| 730 025 | 140 |
| 730 229 | 129 |
| 730 695 | 43 |
| 730 712 | 90 |
| 730 731 | 37 |

7. Hypotensive properties

Administered by intraveinous means to an anaesthetised rat, the derivatives of formula I provoke a lowering of the arterial pressure.

By way of example, the following Table VIII mentions the results obtained by administration of different derivatives of formula I.

TABLE VIII

| Code No. of derivative tested | Dose administered (mg/kg/i.v.) | Percentage reduction of arterial pressure of anaesthetised rate % | Duration of effect (mn) |
|---|---|---|---|
| 72 327 | 1 | 30 | 30 |
| 72 442 | 1 | 30 | 20 |
| 740 140 | 1 | 40 | 30 |
| 730 241 | 2 | 24 | 30 |
| 730 731 | 1 | 29 | 30 |

8. Cardiac properties

These properties are shown by an augmentation of the force of contractions (positive inotrope action) on the isolated heart of a guinea-pig maintained in a conserving medium and under appropriate experimental conditions.

Also, the derivatives of Code Nos. 72419 and 730218 added to the conserving medium, in a concentration of 1 $\mu$g/ml and 0.5 $\mu$g/ml, respectively, exert a positive inotrope action on the isolated heart of the guinea-pig. Additionally, the derivative of Code No. 730 712 added to the conserving medium in a concentration of 1 $\mu$g/ml, permit an augmentation of 140% in the force of contractions on the isolated heart of the guinea- pig.

9. Analgesic properties

The derivatives of formula I administered by oral means to the mouse, are capable of reducing the number of painful stretchings caused by the intraperitoneal injection of phenylbenzoquinone, acetic acid or bradykinine and can potentialise the analagesic action of dextromoramide in the Eddy test. Administered by oral means to the rat, they protect the animal against crying and jumping in the Randall and Selitto test.

By way of example:

the following table IX shows the results obtained by administration of different derivatives of formula I, these results being estimated by the DE 50 of the derivatives and compared to those following administration of:

amidopyrine or 4-dimethylamino-2,3-dimethyl-1 phenyl-3-pyrazolin-5-one of
  glaphenine or N- (7-chloro-4-quinolyl) anthranilic acid 2,3-dihydroxypropyl ester and of
  acetylsalicylic acid
these products being well-known analgesics, and, table X shows the percentages of diminution of the number of painful stretchings observed following the administration of 100 mg/kg/Po of different derivatives.

Moreover, the derivatives of formula I, administered rectally to a rabbit, enabled the pain threshold to be raised in the dentary pulp stimulation test.

As an example, the following table XI gives the results of a comparative study between the activity of derivative code number 730 229 and that of glaphenine, the activities being estimated by the dentary stimulation test.

TABLE IX

| Nature of tests effected | Compound tested | | 105 DE (mg/kg/PO) | DE 50 (mg/kg/PO) | DE 50 / DL 50 |
|---|---|---|---|---|---|
| Test with phenylbenzo quinone | Compounds according to the invention of Code No. | 730 731 | 27 | >>2 000 | <<$1,5.10^{-2}$ |
| | | 730 218 | 37 | 1 500 | $2,5.10^{-2}$ |
| | | 730 224 | 30 | >>2 000 | <<$1,5.10^{-2}$ |
| | | 730 225 | 42 | >2 000 | <$2 .10^{-2}$ |
| | | 730 229 | 10 | 2 800 | $4.10^{-3}$ |
| | | 730 231 | 27 | 975 | $3.10^{-2}$ |
| | | 730 262 | 52 | 2 500 | $2.10^{-2}$ |
| | | 730 732 | 23 | >>2 000 | <<$1.10^{-2}$ |
| | | 740 140 | 33 | >>2 000 | <<$1,5.10^{-2}$ |
| | Reference compounds | amidopyrine | 45 | 1 050 | $4,5.10^{-2}$ |
| | | glaphenine | 60 | 1 900 | $3.10^{-2}$ |
| | | acetylsalicyclic acid | 72 | 700 | $10^{-1}$ |
| Test with bradykinine | Compounds according to the invention of Code No. | 730 229 | 45 | 2 800 | $1,5.10^{-2}$ |
| | | 730 262 | 100 | 2 500 | $4.10^{-2}$ |
| | Reference Compounds | amidopyrine | 48 | 1 050 | $5.10^{-2}$ |
| | | glaphenine | 48 | 1 900 | $2,5.10^{-2}$ |
| | | acetylsalicyclic acid | 180 | 700 | $2,5.10^{-1}$ |
| Test with acetic acid | Compounds according to the invention of Code No. | 730 229 | 70 | 2 800 | $2,5.10^{-2}$ |
| | Reference compounds | amidopyrine | 80 | 1 050 | $7,5.10^{-2}$ |
| | | galphenine | 80 | 1 900 | $4.10^{-2}$ |
| | | acetylsalicyclic acid | 115 | 700 | $1,5.10^{-1}$ |
| Eddy test | Compounds according to the invention of Code No. | 730 218 | 50 | 1 500 | $3,25.10^{-2}$ |
| | | 730 225 | 80 | >>2 000 | <<$4.10^{-2}$ |
| | | 730 229 | 23 | 2 800 | $8.10^{-2}$ |
| | | 730 262 | 60 | 2 500 | $2,5.10^{-2}$ |
| | Reference compounds | amidopyrine | 35 | 1 050 | $3,25.10^{-2}$ |
| | | glaphenine | Unactif with 400 | 1 900 | |
| | | acetylsalicyclic acid | >200 (40 % with 200) | 700 | >$2,75.10^{-1}$ |
| Randall and Selitto test | Compounds according to the invention of Code No. | 730 229 | 45 | 2 800 | $1,5.10^{-2}$ |
| | | amidopyrine | 110 | 1 050 | $1.10^{-1}$ |
| | Reference compounds | glaphenine | 65 | 1 900 | $3,25.10^{-2}$ |
| | | acetylsalicyclic acid | 110 | 700 | $1,5.10^{-1}$ |

TABLE X

| Nature of test effected | Code numero of derivative tested | Dose adminis. (mg/kg/PO) | Percentage of diminution of the number of painful stretchings |
|---|---|---|---|
| | 730 712 | 100 | 60 |
| | 730 695 | 100 | 85 |
| | 730 136 | 100 | 46 |
| | 730 241 | 100 | 67 |
| | 730 282 | 100 | 73 |

TABLE X-continued

| Nature of test effected | Code numero of derivative tested | Dose adminis. (mg/kg/PO) | Percentage of diminution of the number of painful stretchings |
|---|---|---|---|
| Test with phenyl-benzoquinone | 730 283 | 100 | 57 |
| | 72 442 | 100 | 70 |
| | 72 462 | 100 | 40 |
| | 72 608 | 100 | 55 |
| | 72 686 | 130 | 50 |
| | 72 701 | 100 | 45 |
| | 730 234 | 100 | 55 |
| Test with bradykinine | 730 218 | 100 | 40 |
| Randall and Selitto test | 730 225 | 100 | 50 |

TABLE XI

| Compound tested | Dose adm. (mg/kg/ rectally) | DL 50 (mg/kg/PO) | Dose adm. / DL 50 | Number of rabbits whose pain threshold is increased by 0,5 V | Average increase of pain threshold at the peak of activity | Peak of action | Duration of action (hours) |
|---|---|---|---|---|---|---|---|
| Compounds according to the invention of Code Numero | 730 229 | 50 | 2 800 | $2.10^{-2}$ | 7/10 | +2,9 | 1 h | 2 |
| Compound tested | glaphenine | 50 | 1 900 | $2,5.10^{-2}$ | 4/10 | +0,63 | | 1 |
| | | 100 | 1 900 | $5.10^{-2}$ | 6/10 | +1,4 | 45 mn | 1,5 |
| | | 200 | 1 900 | $1.10^{-1}$ | 8/10 | +1,5 | | 2 |

Tables IX and X clearly show that the compounds of the invention show an analgesic activity superior to that of amidopyrine, glaphenine and acetylsalicylic acid since, to obtain the same effect it is enough to administer them in a dose representing a lesser fraction of the lethal dose.

10. Myorelaxant properties

The derivatives of formula I, preventively administered by oral means to the mouse, reduce the mortality caused by the sub-cutaneous injection of strychnine.

Thus, the derivative of Code No. 72608, administered in a dose of 100 mg/kg/p.o., permits a 50 % protection against the lethality of strychnine.

11. Spasmolytic properties

The derivatives of formula I introduced in the conserving medium, are capable of opposing the contractural action of barium chloride in the isolated duodenum of the rat. This activity is evaluated taking papaverine as standard.

Thus, the derivative of Code No. 730 282 presents a spasmolytic activity double to that of papaverine.

12. Antiinflammatory properties

These properties are shown by a diminution of the local oedema caused by the sub-plantar injection of a phlogogenic agent, such as carraghenine, in the rat following the oral administration of derivatives of formula I.

By way of example, the results obtained by the administration of different derivatives of formula I are listed in the following table XII.

Table XIII, as far as it is concerned, gives the results of a comparative study between the antiinflammatory activity of derivative of Code No. 730 229, on the one hand, and the antiinflammatory activity of amidopyrine, glaphenine and acetylsalicylic acid, on the other hand, these reference compounds being those employed in the comparative study of the analgesic properties.

TABLE XII

| Code Numero of derivative tested | Dose administered (mg/kg/PO) | Percentage reduction of subplantar oedema |
|---|---|---|
| 71 510 | 100 | 40 |
| 72 255 | 100 | 60 |
| 72 271 | 100 | 35 |
| 72 283 | 100 | 40 |
| 72 311 | 100 | 50 |
| 72 317 | 100 | 35 |
| 72 327 | 100 | 35 |
| 72 419 | 100 | 50 |
| 72 432 | 100 | 45 |
| 72 442 | 100 | 55 |
| 72 462 | 100 | 35 |
| 72 536 | 100 | 35 |
| 72 686 | 25 | 35 |
| 72 773 | 100 | 40 |
| 72 826 | 100 | 60 |
| 730 234 | 100 | 35 |
| 730 243 | 100 | 50 |

TABLE XIII

| Compound tested | | DE 50 (mg/kg/PO) | DL 50 (mg/kg/PO) | DE 50 / DL 50 |
|---|---|---|---|---|
| Compound according to the invention of Code Numero | 730 229 | 22 | 2 800 | $8.10^{-3}$ |
| Reference compounds | amidopyrine | 140 | 1 050 | $1,25.10^{-1}$ |
| | glaphenine | 9 | 1 900 | $5.10^{-3}$ |
| | acetylsali- | 40 | 700 | $6.10^{-2}$ |

TABLE XIII-continued

| Compound tested | DE 50 (mg/kg/PO) | DL 50 (mg/kg/PO) | DE 50 / DL 50 |
|---|---|---|---|
| cylic acid | | | |

Table XIII shows that the compound of code numero 730 229 possess a notable antiinflammatory activity, since clearly superior to that of amidopyrine and acetylsalicylic acid, and hardly inferior to that of glaphenine.

As a result of a comparison between the pharmacologically active doses mentioned above, and the lethal doses listed in the following table XIV, the difference between the doses is sufficiently great to permit the utilisation of the derivatives of formula I in therapeutics.

TABLE XIV

| Code Numero of derivative tested | Dose administered to the mouse (mg/kg/PO) | Percentage mortality (%) |
|---|---|---|
| 730 732 | 2 000 | 0 |
| 730 218 | 1 500 | ≃50 |
| 730 136 | 2 000 | 0 |
| 730 221 | 520 | ≃50 |
| 730 224 | 2 000 | 0 |
| 730 225 | 2 000 | ≃20 |
| 730 229 | 2 800 | ≃50 |
| 730 231 | 975 | ≃50 |
| 730 241 | 2 000 | 0 |
| 730 379 | 625 | ≃50 |
| 730 262 | 2 500 | ≃50 |
| 730 282 | 1 000 | ≃50 |
| 730 283 | 1 000 | ≃50 |
| 730 243 | 1 000 | 0 |
| 730 695 | 2 000 | 0 |
| 730 712 | 2 000 | 0 |
| 730 731 | 2 000 | 0 |
| 730 741 | 1 500 | ≃50 |
| 740 140 | 2 000 | 0 |
| 71 510 | 2 000 | 0 |
| 72 255 | 2 000 | 0 |
| 72 257 | 2 000 | 0 |
| 72 260 | 2 000 | 0 |
| 72 271 | 2 000 | 0 |
| 72 276 | 2 000 | 0 |
| 72 283 | 2 000 | 0 |
| 72 292 | 2 000 | 0 |
| 72 311 | 2 000 | 0 |
| 72 317 | 2 000 | 0 |
| 72 327 | 2 000 | 0 |
| 72 417 | 2 000 | 0 |
| 72 419 | 2 000 | 0 |
| 72 432 | 2 000 | 0 |
| 72 442 | 2 000 | 0 |
| 72 450 | 2 000 | 0 |
| 72 462 | 2 000 | 0 |
| 72 495 | 2 000 | 0 |
| 72 502 | 2 000 | 0 |
| 72 505 | 2 000 | 0 |
| 72 536 | 2 000 | 0 |
| 72 613 | 2 000 | 0 |
| 72 623 | 2 000 | 0 |
| 72 686 | 2 000 | 0 |
| 72 687 | 2 000 | 0 |
| 72 701 | 2 000 | 0 |
| 72 754 | 2 000 | 0 |
| 72 778 | 2 000 | 0 |
| 72 783 | 2 000 | 0 |
| 72 796 | 2 000 | 0 |
| 72 826 | 2 000 | 0 |
| 730 025 | 2 000 | 0 |
| 72 621 | 2 000 | ≃30 |
| 72 773 | 2 000 | ≃20 |
| 72 608 | 1 600 | ≃50 |
| 730 234 | 2 400 | ≃50 |

The derivatives of formula (I) are useful in the treatment of gastro-duodenal ulcers, dedemas, anxiety, nervousness, contractions, inflammatory pains and diverse originating pains, cardiac insufficiencies, circulatory insufficiencies, asthma, viscoral spasms and according to the product, hypotension or hypertension.

They may be administered by oral means, in the form of tablets, gelules and dragees, containing 25 to 400 mg of active ingredient (1 to 6 times per day), or suspensions containing 0.2 to 5% of active ingredient (10 to 100 drops, 1 to 3 times per day), by parenteral means in the form of injectable ampoules containing 10 to 15C mg of active ingredient (1 to 3 times per day) and by rectal means in the form of suppositories containing 25 to 300 mg of active ingredient (1 to 3 times per day).

Accordingly the present invention also relates to a therapeutic composition comprising a derivative of the general formula (I) together with a therapeutically acceptable carrier.

What we claim is:
1. A compound having the formula

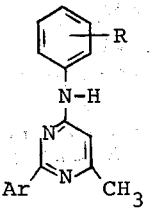

wherein Ar is phenyl or phenyl substituted by a halogen, or a trifluoromethyl, or a methylenedioxy, or one or more methoxy, or an alkyl having one to 4 carbon atoms or a dimethylamino, and wherein R is

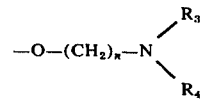

wherein $n$ is an integer from 1 to 5, and $R_3$ and $R_4$ each is alkyl having one to 3 carbon atoms, or

is morpholino, pyrrolidino, piperidino or hexamethyleneimino.

2. A compound as claimed in claim 1, in which Ar is phenyl and

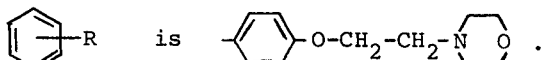

3. A compound as claimed in claim 1, in which Ar is phenyl and the symbol

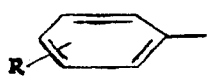

is one of the following:
4-dimethylaminoethoxyphenyl, 4-di(n-propyl)-aminoethoxyphenyl, 4-pyrrolidinoethoxyphenyl, 4-piperidinoethoxyphenyl, 4-morpholinoethoxyphenyl, 2-morpholinoethoxyphenyl, 3-morpholinoethoxyphenyl, 4-hexamethyleneiminoethoxyphenyl and 4-morpholinopropoxyphenyl.

4. A compound as claimed in claim 1 in which Ar is 3-chlorophenyl and the symbol

is one of the following:
4-dimethylaminoethoxyphenyl, 4-hexamethyleneiminoethoxyphenyl and 4-morpholinoethoxyphenyl.

5. A compound as claimed in claim 1, in which Ar is a 4-chlorophenyl and the symbol

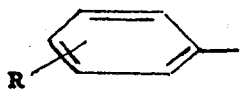

is one of the following:
4-dimethylaminoethoxyphenyl and 4-morpholinoethoxyphenyl.

6. A compound as claimed in claim 1, in which Ar is 3-fluorophenyl and the symbol

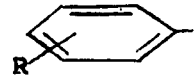

is one of the following:
4-dimethylaminoethoxyphenyl, 4-piperidinoethoxyphenyl, and 4-morpholinoethoxyphenyl.

7. A compound as claimed in claim 1, in which Ar is 3-trifluoromethylphenyl and the symbol

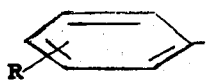

is one of the following:
4-dimethylaminoethoxyphenyl, 4-pyrrolidinoethoxyphenyl and 4-morpholinoethoxyphenyl.

8. A compound as claimed in claim 1, in which Ar is 3,4-methylenedioxyphenyl and the symbol

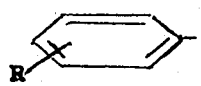

is 4-morpholinoethoxyphenyl.

9. A compound as claimed in claim 1, in which Ar is 3,4,5-trimethoxyphenyl and the symbol

is one of the following:
4-dimethylaminoethoxyphenyl, 4-morpholinoethoxyphenyl, 2-dimethylaminoethoxyphenyl and 2-morpholinoethoxyphenyl.

10. A compound as claimed in claim 1, in which Ar is 4-methoxyphenyl, 4-methylphenyl or 4-dimethylaminophenyl and the symbol

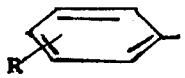

is 4-morpholinoethoxyphenyl.

* * * * *